US010275114B2

(12) United States Patent
Yi et al.

(10) Patent No.: US 10,275,114 B2
(45) Date of Patent: Apr. 30, 2019

(54) MEDICAL IMAGE DISPLAY SYSTEM AND METHOD FOR PROVIDING USER INTERFACE ENABLING THREE-DIMENSIONAL MESH TO BE EDITED ON THREE-DIMENSIONAL VOLUME

(71) Applicant: CORELINE SOFT CO., LTD., Seoul (KR)

(72) Inventors: Jaeyoun Yi, Seoul (KR); Ji Min Kim, Chungcheongbuk-Do (KR); Donghoon Yu, gyeonggi-do (KR)

(73) Assignee: CORELINE SOFT CO., LTD., Seoul (KR)

( * ) Notice: Subject to any disclaimer, the term of this patent is extended or adjusted under 35 U.S.C. 154(b) by 0 days.

(21) Appl. No.: 15/609,785

(22) Filed: May 31, 2017

(65) Prior Publication Data
US 2017/0357406 A1 Dec. 14, 2017

(30) Foreign Application Priority Data
May 31, 2016 (KR) ........................ 10-2016-0067139

(51) Int. Cl.
*A61B 6/00* (2006.01)
*G06T 15/08* (2011.01)
(Continued)

(52) U.S. Cl.
CPC .......... *G06F 3/04815* (2013.01); *A61B 6/463* (2013.01); *A61B 6/466* (2013.01);
(Continued)

(58) Field of Classification Search
None
See application file for complete search history.

(56) References Cited

U.S. PATENT DOCUMENTS 7,309,230 B2 12/2007 Wen
7,728,848 B2 6/2010 Petrov et al.
(Continued)

FOREIGN PATENT DOCUMENTS

JP 1996-194734 A 7/1996
JP 2003-196326 A 10/2012
(Continued)

*Primary Examiner* — Peter Hoang
(74) *Attorney, Agent, or Firm* — Mintz Levin Cohn Ferris Glovsky and Popeo, P.C.; Kongsik Kim; Derek E. Constantine

(57) ABSTRACT

Disclosed are a computing system and method for displaying medical images. The computing system includes a display, and a processor configured to control image information displayed on the display. The processor includes: a receiving unit configured to receive a medical image of a region of interest (ROI) and to acquire three-dimensional (3D) volume information including segmentation information regarding the ROI of the medical image; a display information generation unit configured to acquire 3D mesh information corresponding to the ROI, and to generate display information in which the 3D mesh information has been overlaid on the 3D volume information in a 3D space including the 3D volume information; and a user interface control unit configured to provide a user menu so that a user can edit the 3D mesh information in the 3D space.

20 Claims, 17 Drawing Sheets

(51) Int. Cl.
    *G06F 3/0481*     (2013.01)
    *G06T 17/10*     (2006.01)
    *G06T 7/00*     (2017.01)
    *G06T 17/20*     (2006.01)
    *G06T 19/20*     (2011.01)
    *G06F 3/0482*     (2013.01)

(52) U.S. Cl.
    CPC .............. *A61B 6/469* (2013.01); *A61B 6/487* (2013.01); *A61B 6/5229* (2013.01); *G06T 7/0014* (2013.01); *G06T 15/08* (2013.01); *G06T 17/10* (2013.01); *G06T 17/20* (2013.01); *G06T 17/205* (2013.01); *G06T 19/20* (2013.01); *G06F 3/0482* (2013.01); *G06T 2210/41* (2013.01); *G06T 2210/62* (2013.01); *G06T 2219/2012* (2013.01); *G06T 2219/2021* (2013.01); *G06T 2219/2024* (2013.01)

(56) References Cited

U.S. PATENT DOCUMENTS

| | | |
|---|---|---|
| 8,907,944 B2 | 12/2014 | Lin et al. |
| 8,942,455 B2 | 1/2015 | Chou et al. |
| 2010/0231590 A1 | 9/2010 | Erceis et al. |
| 2012/0233555 A1 | 9/2012 | Psistakis et al. |
| 2013/0002646 A1* | 1/2013 | Lin ...................... G06T 7/0012 345/419 |
| 2013/0135305 A1 | 5/2013 | Bystrov et al. |
| 2016/0004412 A1* | 1/2016 | Meyer ................... G06F 3/0484 345/581 |
| 2016/0155274 A1* | 6/2016 | Merschon .............. A61B 5/743 345/419 |

FOREIGN PATENT DOCUMENTS

| | | |
|---|---|---|
| KR | 10-2000-0063919 A | 11/2000 |
| KR | 10-2012-0111871 A | 10/2012 |

\* cited by examiner

MEDICAL IMAGE DISPLAY SYSTEM AND METHOD FOR PROVIDING USER INTERFACE ENABLING THREE-DIMENSIONAL MESH TO BE EDITED ON THREE-DIMENSIONAL VOLUME

CROSS-REFERENCE TO RELATED APPLICATION

This application claims under 35 U.S.C. § 119(a) the benefit of Korean Application No. 10-2016-0067139 filed on May 31, 2016, which is incorporated herein by reference.

TECHNICAL FIELD

The present invention relates to a system and method for displaying medical images. More specifically, the present invention relates to a display method for providing a user interface enabling a three-dimensional (3D) mesh to be edited on a 3D volume and a computing system for executing the method.

BACKGROUND ART

Technologies for acquiring medical images via various modalities have been used. A medical image for diagnosis is configured such that a brightness value based on a location inside the image varies depending on the reactivity of a material constituting an organ of a human body, and is acquired by reconstructing a set of pieces of such image information.

There are frequent cases where a 3D volume image reconstructed from the raw data of a medical image of a region of interest (ROI) is used to acquire intuitive, effective information in order to diagnose the ROI.

In order to acquire the final version of a 3D image, the process of optimizing mesh information regarding the surface of the 3D image is gone through. In this case, the process of determining whether the mesh information of the 3D image is satisfactory through projection onto a two-dimensional (2D) version (2D plane) of the medical image and the performance of comparison and confirming or reediting the mesh information of the 3D image based on the result of the comparison is iteratively performed.

U.S. Pat. No. 8,942,455 registered on Jan. 27, 2015 and entitled "2D/3D Image Registration Method" discloses the process of optimizing the mesh information of a 3D image of an object, which is a prior art using registration between 2D and 3D images of an object.

Referring to FIG. 1, in the prior art, a 3D volume image of an anatomical ROI (for example, a heart) is acquired at step 102, and segmentation is automatically or manually performed at step 104. 3D mesh data is acquired through segmentation at step 106. At this point, the 3D mesh data acquired as described above has not yet gone through the verification of whether the data includes clinically useful information. FIG. 1 shows a case where 3D mesh information is used as a basis for registering a fluoroscopic image 108 that is acquired in real time. In other words, only the 3D mesh data does not include sufficient clinical information, and is used as guide information for registering a real-time fluoroscopic image. In this case, a 3D mesh is projected onto a 2D plane and provided in the form of a 2D mask at steps 110a and 110b, the pose of the 3D mesh is updated during the process of registering the 2D mask and the 2D fluoroscopic image with each other at step 112, and the 2D mask is optimized at step 116.

In other words, after the 3D mesh data has been projected onto the 2D plane, it is compared with an image having clinical information. Accordingly, the step of optimizing the 3D mesh data or 2D mask is a time-consuming step that is achieved only when the mask generation step 110a and 110b and the pose update step 112 are iteratively performed. The mask generation step 110a and 110b, the pose update step 112, and the optimization step 116 are each performed in independent display and computing environments. Therefore, a user must suffer from the inconvenience of work while iteratively reciprocating between different display and computing environments until the result of the mask generation step 110a and 110b is optimized at step 116.

In other words, as can be seen from the prior art, the step of optimizing 3D mesh data to include clinically useful information consumes a long period of time. Accordingly, prior arts are configured to iteratively perform the process of projecting a 3D volume and 3D mesh data onto a 2D plane, performing comparison, reconstructing the 3D mesh data, and performing optimization in order to overcome the above-described problem, and thus the problem in which the process is counterintuitive and inefficient remains still.

SUMMARY OF THE DISCLOSURE

The present invention has been conceived to overcome the above-described problems, and an object of the present invention is to provide an intuitive user interface which enables a 3D mesh to be edited and optimized on a 3D image.

An object of the present invention is to provide a user-friendly user interface which can reduce the time required for the optimization of a 3D mesh and which enables a 3D mesh to be edited in a single display environment in an integrated manner.

An object of the present invention is to provide a user interface which provides a means for enabling a 3D mesh to be directly edited on a 3D image, thereby enabling the determination of a clinician to be directly used in the process of optimizing the 3D mesh.

An object of the present invention is to provide a user interface which enables a 3D mesh to be intuitively visualized, thus being effective in aiding a clinician to determine the clinical usefulness of the 3D mesh.

An object of the present invention is to provide a user interface and display method which enable a 3D mesh to be intuitively visualized via various visualization means, thereby facilitating the editing and optimization of the 3D mesh.

According to an aspect of the present invention, there is provided a computing system for displaying medical images, the computing system including: a display; and a processor configured to control image information displayed on the display; wherein the processor includes: a receiving unit configured to receive a medical image of a region of interest (ROI) and to acquire three-dimensional (3D) volume information including segmentation information regarding the ROI of the medical image; a display information generation unit configured to acquire 3D mesh information corresponding to the ROI, and to generate display information in which the 3D mesh information has been overlaid on the 3D volume information in a 3D space including the 3D volume information; and a user interface control unit configured to provide a user menu so that a user can edit the 3D mesh information in the 3D space.

The display information is 3D display information represented in the 3D space, and may represent depth information in the 3D space. The display information may be generated by overlaying the 3D mesh information on the 3D volume information in the 3D space including the 3D volume information. The user menu is provided such that the user can edit the 3D mesh information in the 3D space.

The computing system may generate the display information so that a first portion of the 3D mesh information located outside/outward the 3D volume information can be displayed while having a first visual attribute and a second portion of the 3D mesh information located inside/inward the 3D volume information can be displayed while having a second visual attribute.

The computing system may calculate quantitative information regarding the extent to which a portion of the 3D mesh information has deviated from the 3D volume information, and may assign a visual attribute based on the quantitative information to the portion of the 3D mesh information. The quantitative information may be calculated based on the longest distance by which a vertex of a 3D mesh has been spaced apart from a 3D volume, or may be calculated based on the volume of the first portion that has deviated from the 3D volume information.

The computing system may generate the display information by assigning a first visual attribute and a first transparency to the 3D mesh information and assigning a second visual attribute and a second transparency to the 3D volume information.

The computing system may generate an initialized version of the 3D mesh information based on the 3D volume information.

The computing system may generate the 3D mesh information based on a standard model for organ included in the ROI. In this case, the computing system may use a personalized standard model based on personal information of a patient and disease diagnosis information regarding the organ included in the ROI of the patient as the standard model for the ROI.

The computing system may generate an initialized version of the 3D mesh information based on past diagnosis information regarding the organ included in the ROI of a patient.

The computing system may store a final version of the 3D mesh information or the history of updated versions of the 3D mesh information.

The computing system may generate updated 3D mesh information by means of an input of the user adapted to modify the 3D mesh information and received in response to the user menu, and may generate the display information so that the updated 3D mesh information can be displayed in place of the 3D mesh information.

A method of displaying medical images according to another aspect of the present invention is executed in a computing system including a display and a processor.

The method includes: receiving a medical image of a region of interest (ROI); acquiring three-dimensional (3D) volume information including segmentation information regarding the ROI of the medical image; acquiring 3D mesh information corresponding to the ROI; generating display information in which the 3D mesh information has been overlaid on the 3D volume information; and providing a user menu so that a user can edit the 3D mesh information.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE DISCLOSURE

The above and other objects, features and advantages of the present invention will be more clearly understood from the following detailed description of embodiments taken in conjunction with the accompanying drawings.

The embodiments of the present invention will be described in detail with reference to the accompanying drawings. In the following description of the present invention, a detailed description of a related well-known component or function will be omitted when it is determined that the detailed description may make the gist of the present invention obscure.

The prevent invention is not limited to the embodiments. Throughout the accompanying drawings, the same reference symbols designate the same components.

The embodiments of the present invention are described in detail with reference to the accompanying drawings below.

Figure 2:
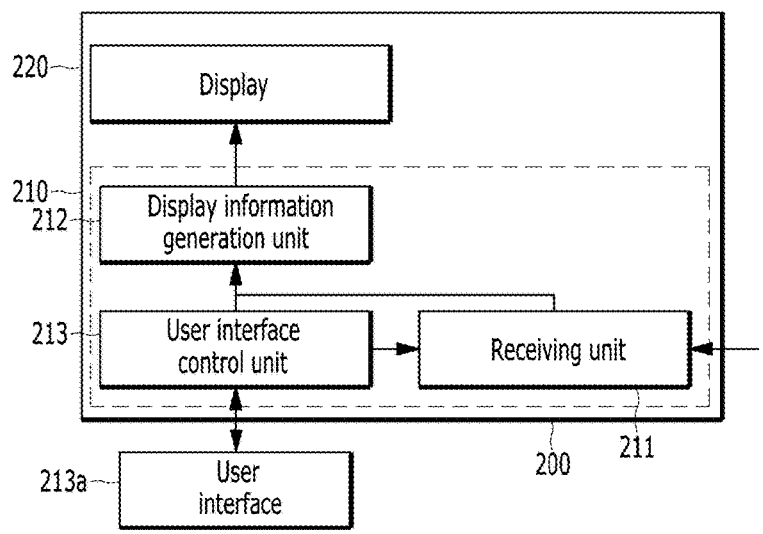
FIG. 2 is a diagram showing a computing system for displaying medical images according to an embodiment of the present invention.

FIG. 2 is a diagram showing a computing system 200 for displaying medical images according to an embodiment of the present invention.

The computing system 200 shown in FIG. 2 includes a processor 210, a display 220, and a user interface 213a. The user interface 213a refers to an interface capable of receiving a command from a user, such as a keyboard, a mouse, a track ball, a touch screen, a microphone, or the like. The processor 210 may control image information displayed on the display 220, and may generate the display attribute or display information of a medical image displayed on the display 220.

Referring to FIG. 2, the processor 210 includes a receiving unit 211, a display information generation unit 212, and a user interface control unit 213. The receiving unit 211 may receive a medical image from external medical imaging diagnostic equipment (a modality). The receiving unit 211 receives a medical image of an ROI whose 3D mesh is to be edited, and may acquire 3D volume information including preliminary segmentation information regarding the ROI of the medical image. The preliminary segmentation of the received medical image may be performed by the processor 210, and may be performed by another external processor or a computing system.

The display information generation unit 212 may acquire 3D mesh information corresponding to the ROI, and may generate display information in which the 3D mesh information has been overlaid on 3D volume information.

Although the 3D mesh information corresponding to the ROI may be generated by the processor 210, previously generated reference mesh information may be acquired from an external reference database.

In the display information according to the present invention, the 3D mesh information is overlaid on the 3D volume information. Accordingly, the medical image and the 3D mesh information can be provided in the state in which a clinician can easily determine whether the 3D mesh information is appropriate to provide clinically useful information.

The 3D volume information is volume information that is obtained by applying a segmentation technique to the raw data of the medical image. The raw data of the medical image is generated in the state in which a brightness value based on the reactivity of a material constituting an organ corresponding to the location of each voxel has been represented in the voxel. The segmentation technique is configured to identify a group of voxels, whose range of brightness values falls within a predetermined reference value, as the same region. In this case, there is a case where the 3D volume information obtained through segmentation has an external shape different from the clinically known features of the anatomical structure of a corresponding ROI for various reasons, such as the environment of the acquisition of a medical image, the characteristics of a modality, the characteristic of a patient, etc. Accordingly, it is necessary to correct such a segmentation result.

Since conventional technologies for editing, adapting or optimizing a 3D segmentation result have complex and difficult processes of acquiring 3D mesh data from a 3D volume, various methods have been proposed to execute the process in a simple manner. In other words, since the conventional technologies have very difficult processes of comparing a 3D volume with 3D mesh data, developments have been made toward comparing 3D mesh data with 2D medical image data, obtained by projecting a 3D volume onto a 2D plane, instead of a 3D volume. A 2D mesh is generated by projecting 3D mesh data onto the reference plane of 2D medical image data, and a clinician verifies the usefulness of the 2D mesh under his or her clinical determination by comparing 2D medical image data with the 2D mesh.

Figure 1:
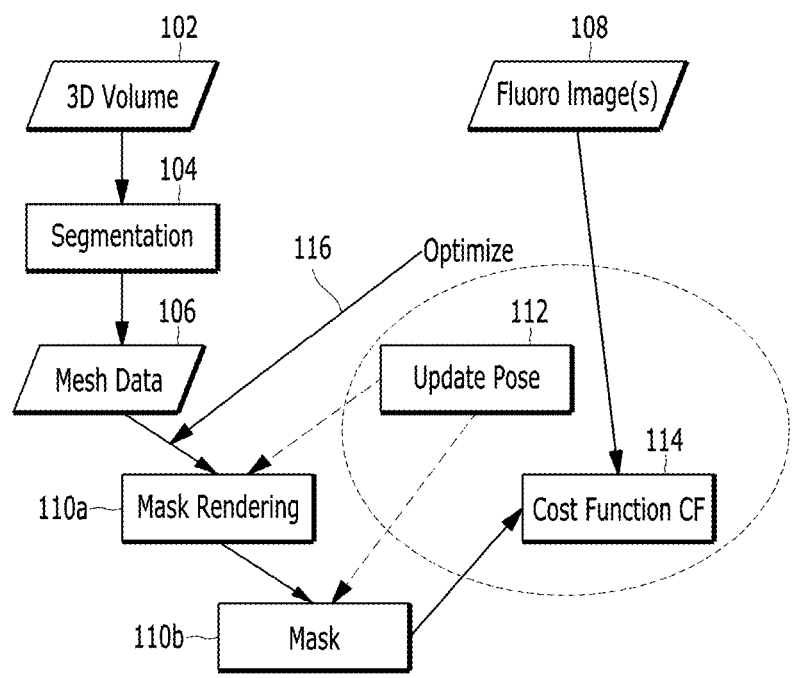
FIG. 1 is a diagram showing the process of using registration between a 2D fluoroscopic image and pre-operative 3D mesh data in order to optimize a 3D mesh according to a prior art.

As shown in the prior art of FIG. 1 above, this method cannot verify the overall shape of a 3D mesh at one time, and a reference plane is dependent on and limited by a reference pose in which a subject is projected. Accordingly, the optimization of mesh data is performed using only a 2D mesh (a version obtained by projecting a 3D mesh onto a 2D plane), which is merely a portion of the 3D mesh, with the result that a problem arises in that massive numbers of trials and errors must be gone through. A user cannot verify all the results of the process of editing a 3D mesh at one time, and thus the user must check matching with anatomical/structural features by using only the information of a portion of a 3D mesh (information projected onto a 2D plane). Accordingly, it is considerably difficult to achieve a final result via signal editing, and the process of editing a mesh is iteratively performed a plurality of times.

In this case, the process of editing a 3D mesh and the process of checking whether the 3D mesh has been edited sufficiently to match the anatomical/structural features of a medical image are performed as independent processes, and are executed in independent programming environments or separate systems. Accordingly, inconvenience occurs in that whenever the process of editing a mesh and the process of checking the result of the editing are performed, data is transferred from an editing system to a checking system, comparison is performed, and then a new editing process is re-executed in the editing system while incorporating the result of the checking of the checking system thereinto.

In the present invention, 3D mesh information is directly overlaid on a 3D medical image, i.e., 3D volume information, thereby providing an effective and intuitive user interface and display screen in which the optimization of 3D mesh information can be performed in a 3D space.

The 3D display information provided in the present invention may have information in the state in which 3D mesh information has been overlaid on 3D volume information in a single 3D space (a 3D space including the 3D volume information), and may have display information in which 3D volume information and 3D mesh information have been represented in an overlaid state by incorporating depth information based on the direction of a view into each pixel. A user can determine the differences between a current version of 3D mesh information and 3D volume information within a short period of time by easily manipulating the viewpoint of 3D display information, and can intuitively check whether the current version of 3D mesh information matches clinically significant anatomical/structural features.

The user interface control unit 213 may provide a user interface (a user menu) via which a user can edit 3D mesh information. In this case, the 3D mesh information is in the state of being overlaid on 3D volume information in a single 3D space. The user can review the 3D volume information (a segmentation result) together with the 3D mesh information in the state in which relative depth information is represented in the 3D space, and thus it becomes considerably easy to edit or adapt the 3D mesh information. In other words, the user menu is a user menu via which the 3D mesh information overlaid and displayed on the 3D volume information can be modified.

The process in which a user modifies 3D mesh information via the user menu may be realized via the process of generating new 3D mesh information by changing the location of at least one vertex included in the 3D mesh information or by proposing a new location at which a new vertex is to be located.

In this case, updated 3D mesh information is generated via an input of the user adapted to modify the 3D mesh information received via the user interface 213a and the user interface control unit 213. The updated 3D mesh information is included in the display information so that the updated 3D mesh information can be displayed in place of the existing 3D mesh information.

According to a first embodiment of the visualization of the 3D mesh information, the display information generation unit 212 may generate display information so that the first portion of the 3D mesh information located outside/outward the 3D volume information when depth information is taken into account in a single 3D space and a second portion is located inside/inward the space 3D volume information can be displayed while having a first visual attribute and a second visual attribute, respectively. In other words, this embodiment is an embodiment that provides visualization information regarding a portion in which the 3D mesh information does not match the 3D volume information. In this case, a case where the 3D mesh information has further protruded to the outside than the 3D volume information in a 3D space may be determined to be a first portion, and a case where the outer surface of 3D mesh information is located inside 3D volume information in a 3D space may be determined to be a second portion. The first visual attribute and the second visual attribute may refer to visual attributes that are displayed while having different colors, different brightnesses/saturations, or different patterns. In other words, when the 3D volume information generated through preliminary segmentation does not accurately incorporate the anatomical/structural features of an ROI thereinto, the surface of the 3D mesh information is modified to represent the anatomical/structural features, with the result that the outer surface of the 3D mesh information may not match the 3D volume information. The 3D mesh information may be initialized based on the 3D volume information, or may be initialized based on a standard model, such as an atlas, for an ROI.

According to a second embodiment of the visualization of the 3D mesh information, the display information generation unit 212 may calculate quantitative information regarding the extent to which a portion of the 3D mesh information has deviated from the 3D volume information. The display information generation unit 212 may assign a visual attribute based on the quantitative information to the portion of the 3D mesh information that has deviated from the 3D volume information. As described above, the portion of the 3D mesh information may be identified as a first portion when it has protruded out of the 3D volume information, and may be identified as a second portion when it is located inside the 3D volume information. First quantitative information regarding the extent to which the first portion has deviated from the 3D volume information may be calculated based on the longest distance by which a vertex of a 3D mesh of the first portion has been spaced apart from a 3D volume, or may be calculated based on the volume of the first portion. In this case, when a plurality of separate first portions is present, each of the plurality of separate first portions may have unique first quantitative information. In the same manner, second quantitative information regarding the extent to which the second portion has deviated from (has been inserted into) the 3D volume information may be calculated based on the longest distance by which a vertex of a 3D mesh of the second portion has been spaced apart from a 3D volume, or may be calculated based on the volume of the second portion. In this case, when a plurality of separate second portions is present, each of the plurality of separate second portions may have unique first quantitative information.

According to a third embodiment of the visualization of the 3D mesh information, the display information generation unit 212 may generate display information by assigning a third visual attribute and a first transparency to the 3D mesh information and also assigning a fourth visual attribute and a second transparency to the 3D volume information. The third embodiment may be understood to have a form similar to that of the first embodiment. When the third visual attribute and the fourth visual attribute are presented as different colors or different patterns, the first portion in which the 3D mesh information has further protruded than the 3D volume information and the second portion in which 3D mesh information has been located inside the 3D volume information may be represented while having different visual attributes as a result.

A technique for assigning visual attributes to 3D mesh information, which is proposed by the present invention, can directly compare 3D mesh information on a 3D volume and, when the 3D mesh information has been edited, can rapidly examine the influence of the editing on the 3D volume, thereby significantly reducing the time required for the process of optimizing a 3D mesh.

A technique for optimizing 3D mesh information according to the present invention can directly compare a 3D volume with a 3D mesh by assigning visual attributes while taking into account 3D characteristics. The prior art for performing projection onto a 2D plane and comparing a 2D image with a 2D mesh (i.e., the projection of a 3D mesh onto a 2D plane) cannot perform such direct comparison.

According to the first embodiment of the initialization of the 3D mesh information, the display information generation unit 212 may initialize the 3D mesh information based on the 3D volume information (preliminary segmentation information). In this case, the determination of a clinician acts significantly. The 3D mesh information may be modified based on the determination of the clinician, and portions that have deviated from the 3D volume information may occur.

According to the second embodiment of the initialization of the 3D mesh information, the display information generation unit 212 may generate the 3D mesh information based on a standard model of an ROI. When the ROI is a heart, the 3D mesh information may be initialized by enlarging or reducing a standard model of the heart, representing the standard model by using a mesh grid and overlaying the standard model on the 3D volume information.

The display information generation unit 212 may use a standard model obtained by personalizing the standard model of the ROI. In other words, the personalized standard model may be generalized by incorporating the personal information (physical characteristics, such as age, gender, height, weight, and specific immunity) of a patient and disease diagnosis information (the progress of the disease of the organ of the ROI, and the type of disease) for the ROI of the patient thereinto.

According to the third embodiment of the initialization of the 3D mesh information, the display information generation unit 212 may generate an initialized version of the 3D mesh information based on past diagnosis information for the ROI of the patient. The third embodiment will be described with reference to FIG. 3 in greater detail.

Figure 3:
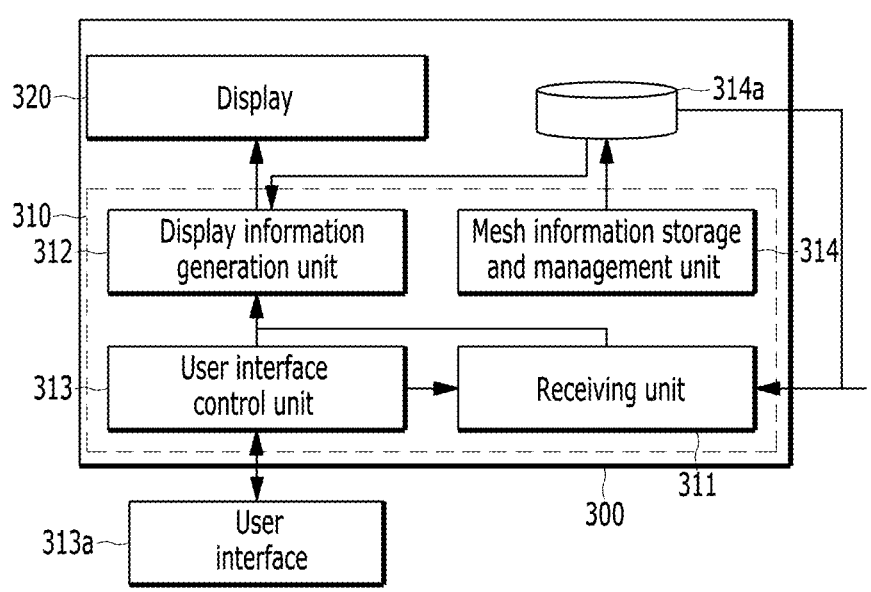
FIG. 3 is a diagram showing a computing system for displaying medical images according to an embodiment of the present invention.

FIG. 3 is a diagram showing a computing system 300 for displaying medical images according to an embodiment of the present invention.

The computing system 300 shown in FIG. 3 includes a processor 310, a display 320, a user interface 313a, and a database 314a. Since the display 320 and user interface 313a shown in FIG. 3 basically perform the same functions as the display 220a and user interface 213a shown in FIG. 2, redundant descriptions thereof are omitted.

Referring to FIG. 3, the processor 310 includes a receiving unit 311, a display information generation unit 312, a user interface control unit 313, and a mesh information storage and management unit 314. The function of the user interface control unit 313 of the processor 310 is the same as that of the user interface control unit 213 shown in FIG. 2.

The mesh information storage and management unit 314 may store the final version of the 3D mesh information or the history of updated versions of the 3D mesh information in the database 314a. The mesh information storage and management unit 314 may store the final version of the 3D mesh information or the history of the updated versions of the 3D mesh information in the database 314a in association with the final version of the 3D mesh information or the history of the updated versions of the 3D mesh information associated with the personal information (physical characteristics, such as age, gender, height, weight, and specific immunity) of a patient and disease diagnosis information (the progress of the disease of the organ of the ROI, and the type of disease) for an ROI of the patient in order to enable the data to be referred to in a future diagnosis process.

In this case, the display information generation unit 312 may generate the initialized version of the 3D mesh information based on past diagnosis information regarding the ROI. In other words, the display information generation unit 312 may download past determined 3D mesh information for the ROI of the patient from the database 314a, and may initialize current 3D mesh information. The user interface control unit 313 may provide a search menu for the past diagnosis information stored in the database 314a. The items that can be searched for via the search menu may be various combinations, such as a combination of the personal information and ROI of a patient, a combination of the personal information and disease type of the patient, a combination of the type and progress of a disease, etc.

Meanwhile, the receiving unit 311 may receive a medical image of the ROI of a patient from an external modality, or may receive a medical image stored in the database 314a. The receiving unit 311 may acquire 3D volume information including segmentation information regarding the ROI of the patient from an external separate computing system, and may acquire 3D volume information stored in the database 314a.

The medical image and the 3D volume information may be transferred to the display information generation unit 312 by the receiving unit 311. The display information generation unit 312 may acquire initialized 3D mesh information, and may generate display information in which the initialized 3D mesh information has been overlaid on the 3D volume information.

Figure 4:
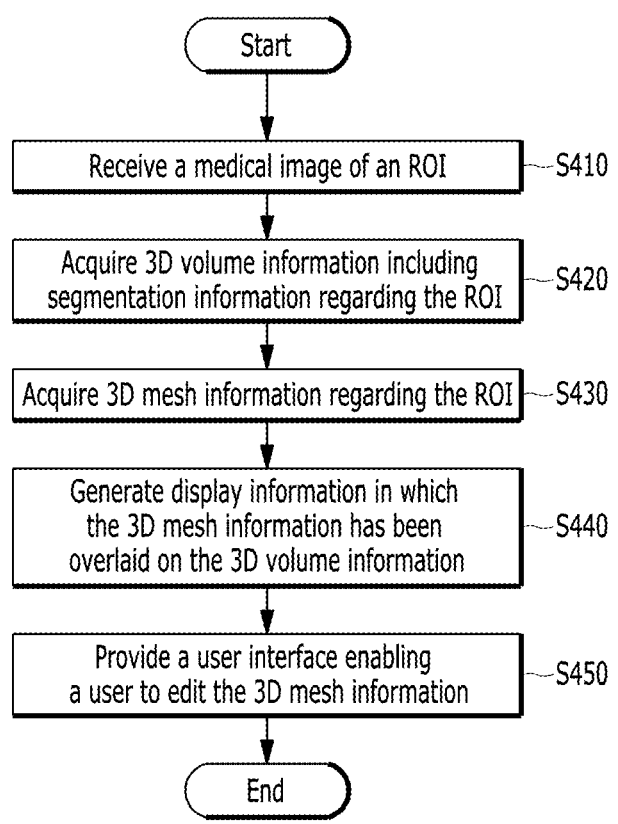
FIG. 4 is an operation flowchart showing a method of displaying medical images according to an embodiment of the present invention.

FIG. 4 is an operation flowchart showing a method of displaying medical images according to an embodiment of the present invention. The method according to the present invention may be executed in a computing system including a processor and a display.

Referring to FIG. 4, the method according to the present invention includes step S410 of receiving a medical image of an ROI.

The method according to the present invention includes step S420 of acquiring 3D volume information including segmentation information regarding the ROI.

The method according to the present invention includes step S430 of acquiring 3D mesh information regarding the ROI.

The method according to the present invention includes step S440 of generating display information in which the 3D mesh information have been overlaid on the 3D volume information.

The method according to the present invention includes step S450 of providing a user menu so that a user can edit the 3D mesh information.

FIGS. 5 to 9 are operation flowcharts showing methods of displaying medical images according to various embodiments of the present invention.

Figure 5:
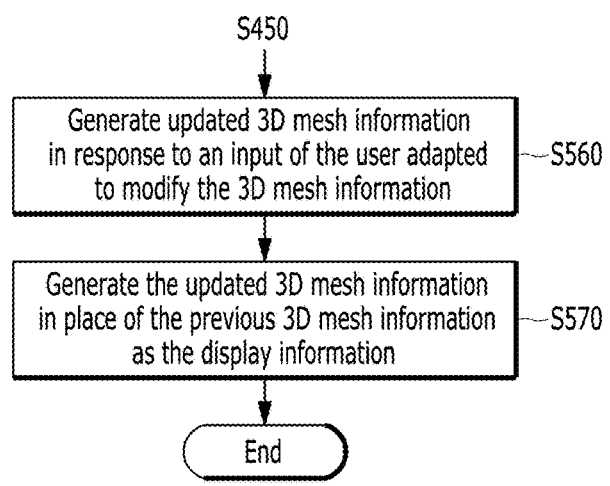
FIGS. 5 to 9 are operation flowcharts showing methods of displaying medical images according to various embodiments of the present invention.

Referring to FIG. 5, this method according to the present invention includes step S560 of generating updated 3D mesh information in response to an input of a user adapted to modify the 3D mesh information after the user menu has been provided at step S450. This method according to the present invention includes step S570 of generating the updated 3D mesh information in place of the previous 3D mesh information as the display information.

Figure 6:
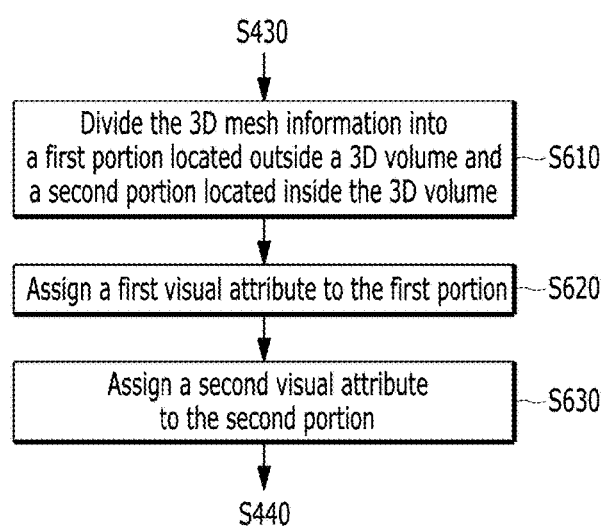

Referring to FIG. 6, this method according to the present invention includes step S610 of dividing the 3D mesh information acquired at step S430 into a first portion located outside/outward the 3D volume and a second portion located inside/inward the 3D volume.

This method according to the present invention includes step S620 of assigning a first visual attribute to the first portion and step S630 of assigning a second visual attribute to the second portion. This method according to the present invention includes step S440 of generating display information by using the first visual attribute assigned to the first portion of the 3D mesh information and the second visual attribute assigned to the second portion.

Figure 7:
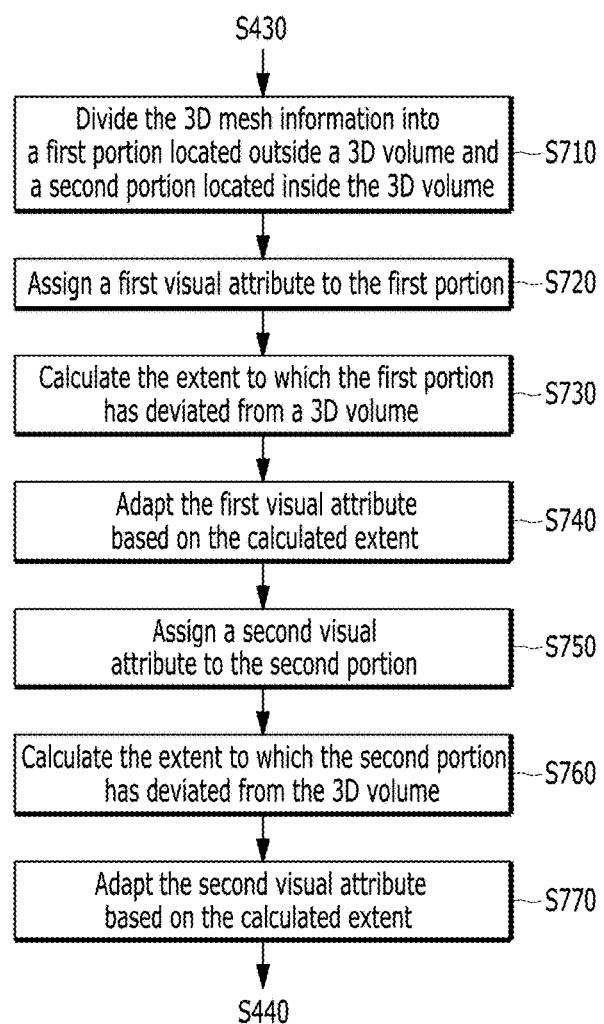

Steps S710 and S720 shown in FIG. 7 are the same as steps S610 and S620 shown in FIG. 6, and step S750 shown in FIG. 7 is the same as step S630 shown in FIG. 6.

Referring to FIG. 7, this method according to the present invention includes step S730 of calculating information about the extent to which the first portion has deviated from the 3D volume. This method according to the present invention includes step S740 of adapting the first visual attribute by using first quantitative information calculated for the first portion. In other words, when a plurality of first portions is present, each of the plurality of first portions has a unique first visual attribute adapted based on each piece of first quantitative information.

This method according to the present invention includes step S760 of calculating information about the extent to which the second portion has deviated from the 3D volume. This method according to the present invention includes step S770 of adapting the second visual attribute by using second quantitative information calculated for the first portion. In other words, when a plurality of second portions is present, each of the plurality of second portions has a unique second visual attribute adapted based on each piece of second quantitative information.

Figure 8:
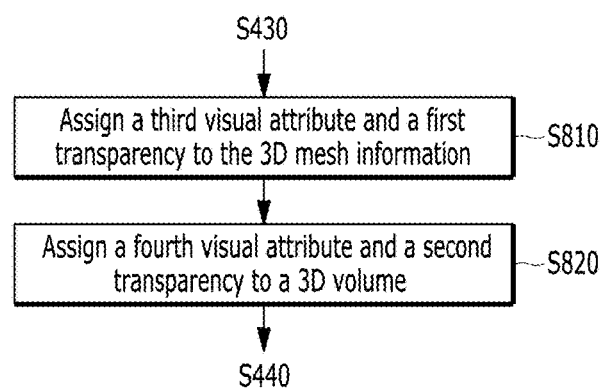

Referring to FIG. 8, this method according to the present invention includes step S810 of assigning a third visual attribute and a first transparency to the 3D mesh information and step S820 of assigning a fourth visual attribute and a second transparency to the 3D volume.

Figure 9:
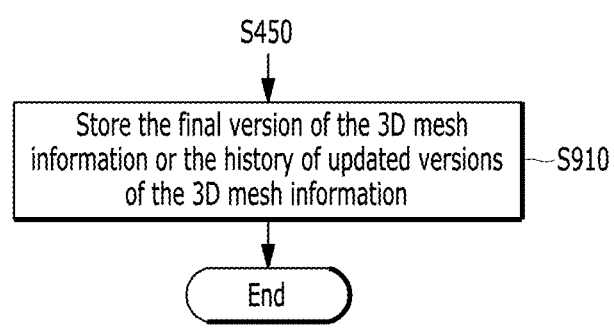

Referring to FIG. 9, this method according to the present invention may further include step S910 of storing a final version of the 3D mesh information or the history of the updated versions of the 3D mesh information.

Figure 10:
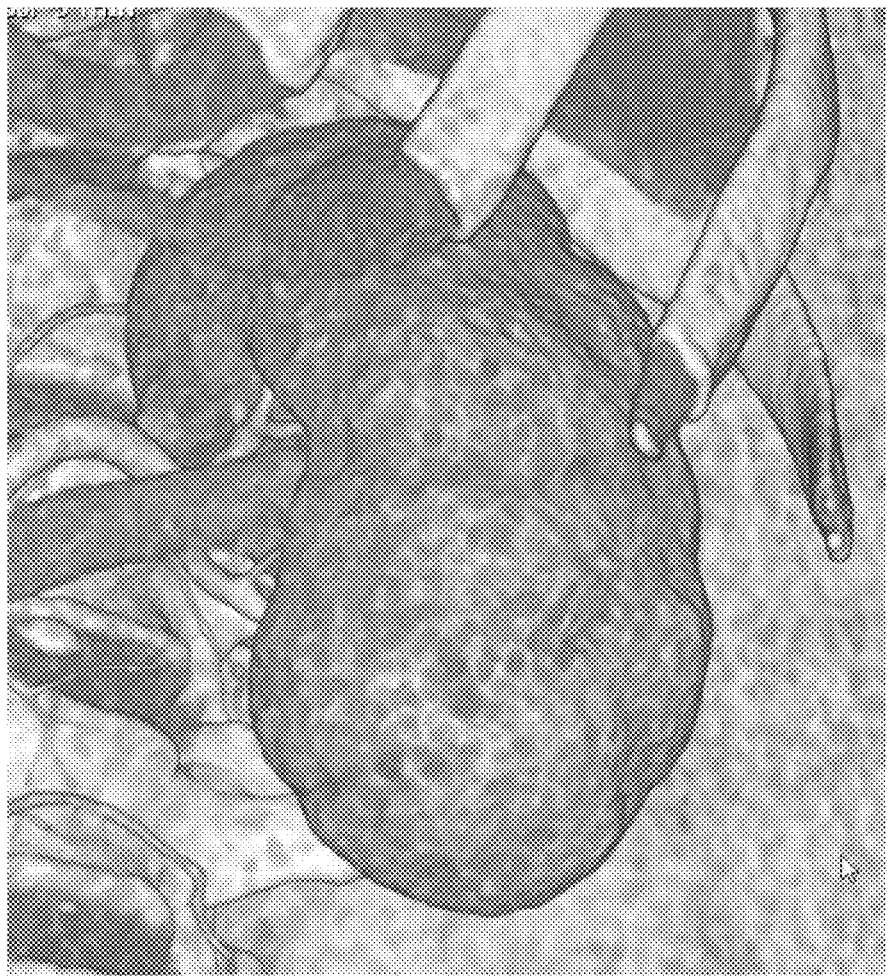
FIG. 10 is a view showing the 3D volume information of a medical image according to an embodiment of the present invention.

FIG. 10 is a view showing the 3D volume information of a medical image according to an embodiment of the present invention. The 3D volume information of FIG. 10 may be obtained by applying a volume rendering technique, well known to those skilled in the art, to the medical image obtained by a modality.

Figure 11:
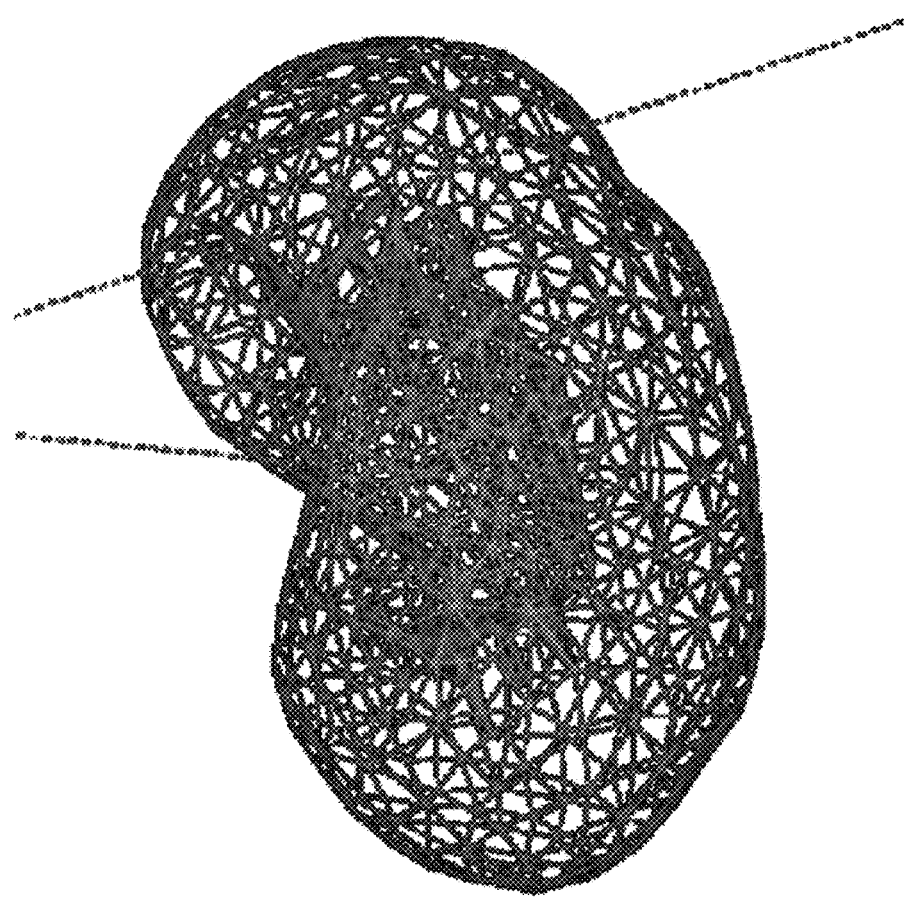
FIG. 11 is a view showing the 3D mesh information of the medical image according to an embodiment of the present invention.

FIG. 11 is a view showing the 3D mesh information of the medical image according to an embodiment of the present invention. The 3D mesh information of FIG. 11 may be obtained by applying a surface rendering technique, known to those skilled in the art, to the medical image obtained by a modality.

Figure 12:
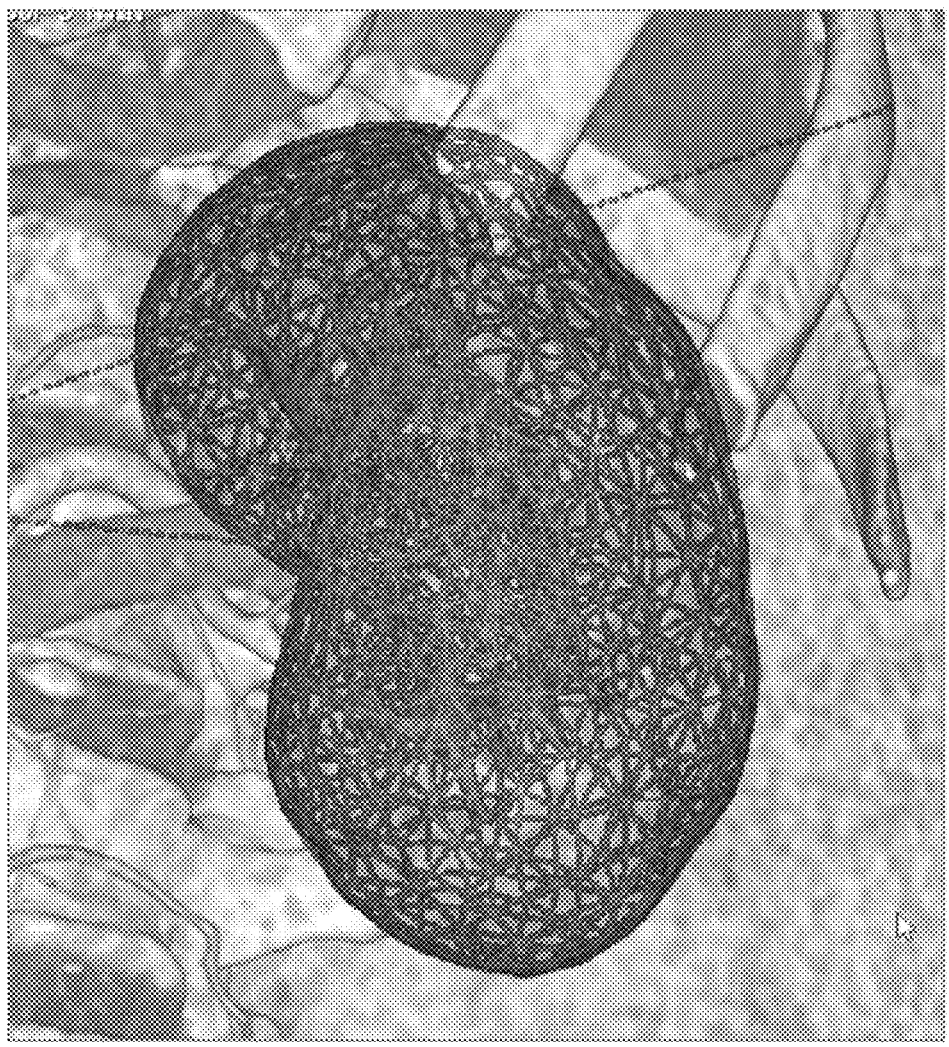
FIG. 12 is a view showing an example in which the 3D mesh information of FIG. 11 has been simply overlaid on the 3D volume information of FIG. 10 according to a related art.

FIG. 12 is a view showing an example in which the 3D mesh information of FIG. 11 has been simply overlaid on the 3D volume information of FIG. 10 according to a related art. In FIG. 12, the 3D mesh information of FIG. 11 replaces the 3D volume information of FIG. 10 represented by individual pixels and the pixel values of the 3D volume information of FIG. 10 and the pixel values of the 3D mesh information of FIG. 11 are simply added to each other or subtracted from each other, and thus display information is generated in the state in which space information or depth information depth information has been lost. Referring to FIG. 12, the 3D volume information of FIG. 10 is substantially covered with the 3D mesh information of FIG. 11, and thus it is difficult to determine the relationship between the relative locations of the 3D mesh information and the 3D volume information.

Figure 13:
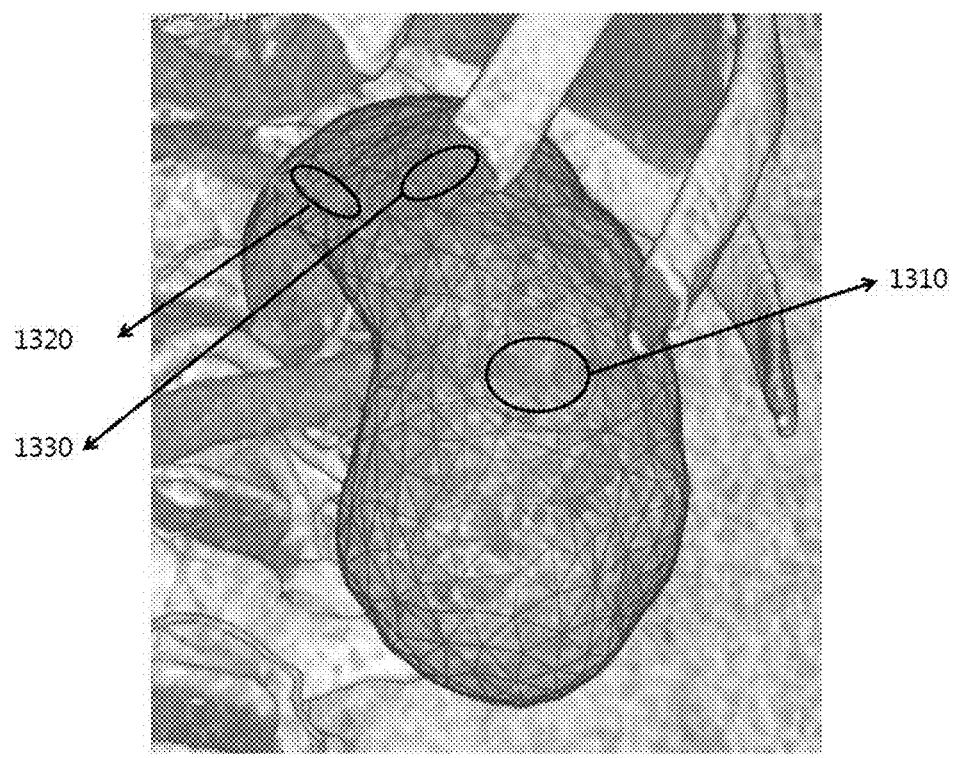
FIG. 13 is a view showing an example of display information that is generated such that depth information in a 3D space can be represented by overlaying the 3D mesh information of FIG. 11 on the 3D volume information of FIG. 10 in a 3D space including the 3D volume information according to an embodiment of the present invention.

FIG. 13 is a view showing an example of display information that is generated such that depth information in a 3D space can be represented by overlaying the 3D mesh information of FIG. 11 on the 3D volume information of FIG. 10 in the 3D space including the 3D volume information according to an embodiment of the present invention.

According to FIG. 13, the 3D volume information of FIG. 10 and the 3D mesh information of FIG. 11 are displayed together in a single 3D space in the state of being overlaid on each other while maintaining the depth information of each of them. In other words, in the direction of the view, first regions 1310, 1320 and 1330 in which the 3D volume information of FIG. 10 has closer depth information than the 3D mesh information of FIG. 11 are shown. In these first regions 1310, 1320 and 1330, the 3D mesh information is placed inside the boundary surface of the 3D volume information. In the region exclusive of the first regions 1310, 1320 and 1330, the 3D mesh information is located outside the boundary surface of the 3D volume information.

When the transparency of the 3D volume information is increased higher than that of FIG. 13, an adaptation may be made such that faint 3D mesh information can be represented in the first regions 1310, 1320 and 1330. In this case, a user menu adapted to enable 3D mesh information to be modified may be provided such that a user can match the boundary surface of the 3D mesh information and the boundary surface of 3D volume information to each other by modifying the 3D mesh information of the first regions 1310, 1320 and 1330.

In the remaining region exclusive of the first regions 1310, 1320 and 1330, a user menu adapted to enable a 3D mesh to be modified without adapting transparency may be provided. A user may input a user command to match the boundary surface of the 3D mesh information and the boundary surface of the 3D volume information with each other by modifying the 3D mesh information in response to the user menu.

Figure 14:
FIG. 14 is a view showing the 3D volume information of the medical image according to another embodiment of the present invention.

FIG. 14 is a view showing the 3D volume information of the medical image according to another embodiment of the present invention.

Figure 15:
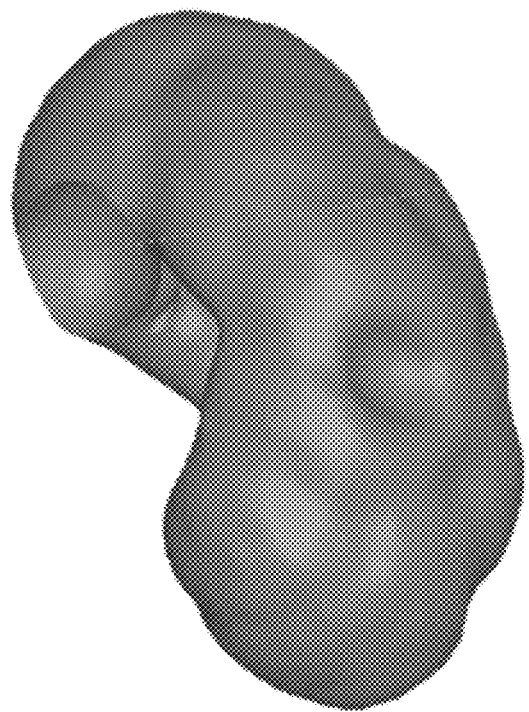
FIG. 15 is a view showing the 3D mesh information of the medical image according to another embodiment of the present invention.

FIG. 15 is a view showing the 3D mesh information of the medical image according to another embodiment of the present invention. FIG. 15 shows a case where the display information of 3D mesh information has been changed from a mesh type to an opaque and continuous display type.

Figure 16:
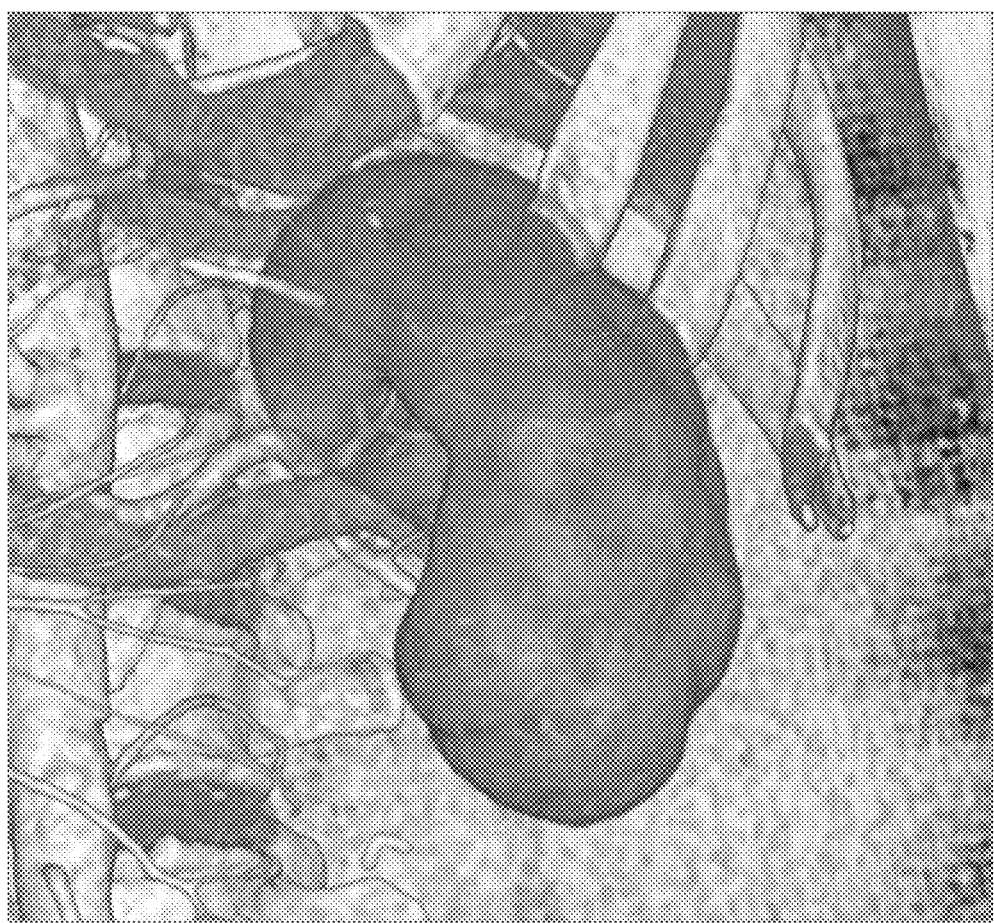
FIG. 16 is a view showing an example in which the 3D mesh information of FIG. 15 has been simply overlaid on the 3D volume information of FIG. 14 according to a related art.

FIG. 16 is a view showing an example in which the 3D mesh information of FIG. 15 has been simply overlaid on the 3D volume information of FIG. 14 according to a related art.

In FIG. 16, the 3D volume information of FIG. 14 is covered with the 3D mesh information of FIG. 15 and thus it is difficult to determine the relationship between the relative locations of the 3D mesh information and the 3D volume information, as in FIG. 12.

Figure 17:
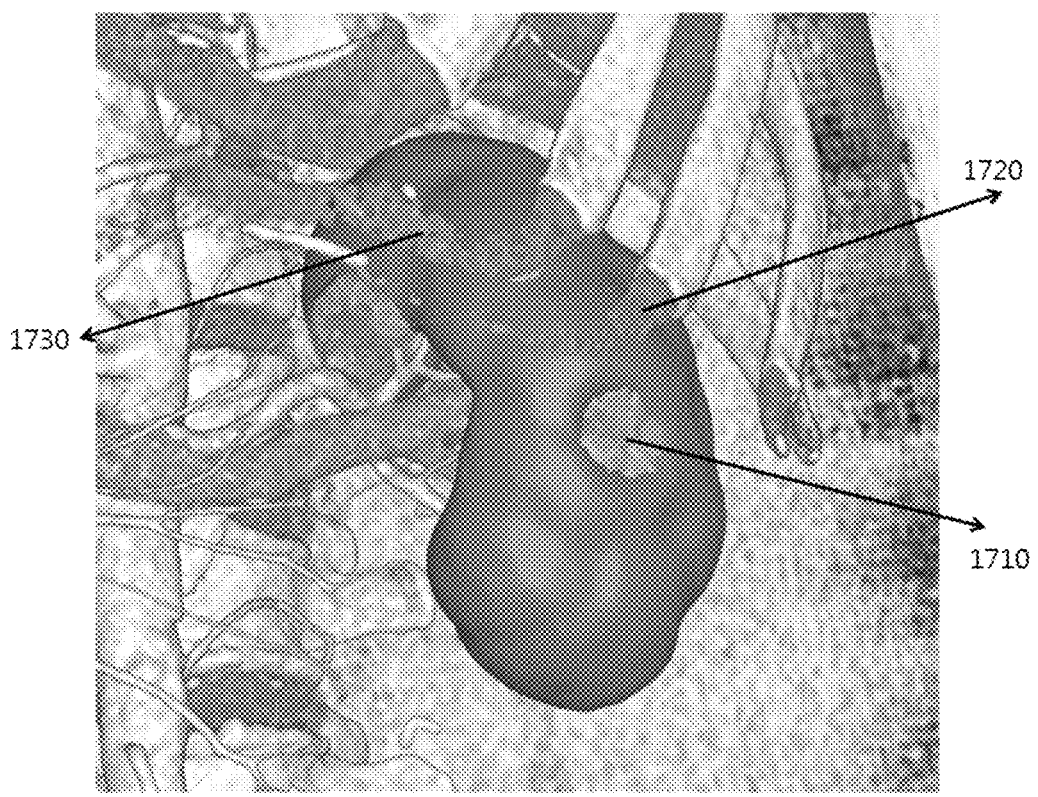
FIG. 17 is a view showing another example of display information that is generated such that depth information in a 3D space can be represented by overlaying the 3D mesh information of FIG. 15 on the 3D volume information of FIG. 14 in the 3D space including the 3D volume information according to another embodiment of the present invention.

FIG. 17 is a view showing another example of display information that is generated such that depth information in a 3D space can be represented by overlaying the 3D mesh information of FIG. 15 on the 3D volume information of FIG. 14 in the 3D space including the 3D volume information according to another embodiment of the present invention.

According to FIG. 17, the relative depth information between a 3D volume and a 3D mesh is represented in the 3D space, and thus which of a 3D volume and a 3D mesh is exposed out of a boundary surface is represented for each pixel.

FIG. 17 indicates that the boundary surface of the 3D volume is located outside the 3D mesh in second regions 1710, 1720 and 1730. A user may acquire the state in which the relationship between the locations of the 3D mesh and the 3D volume can be intuitively and easily determined by adapting the display options (transparency, color, and/or pattern) of the 3D mesh.

For example, in the display options shown in FIG. 17, the relationships between the relative depths and locations of the 3D volume and the 3D mesh may be intuitively and easily understandable. Thereafter, a display that enables a user to more easily modify a 3D mesh may be selected by selecting the display options shown in FIG. 13.

Each of the methods according to the embodiments of the present invention may be implemented in the form of program instructions that can be executed by a variety of computer means, and may be stored in a computer-readable storage medium. The computer-readable storage medium may include program instructions, a data file, and a data structure solely or in combination. The program instructions that are stored in the medium may be designed and constructed particularly for the present invention, or may be known and available to those skilled in the field of computer software. Examples of the computer-readable storage medium include magnetic media such as a hard disk, a floppy disk and a magnetic tape, optical media such as CD-ROM and a DVD, magneto-optical media such as a floptical disk, and hardware devices particularly configured to store and execute program instructions such as ROM, RAM, and flash memory. Examples of the program instructions include not only machine language code that is constructed by a compiler but also high-level language code that can be executed by a computer using an interpreter or the like. The above-described hardware components may be configured to act as one or more software modules that perform the operation of the present invention, and vice versa.

According to the present invention, there can be provided an intuitive user interface which enables a 3D mesh to be edited and optimized on a 3D image.

According to the present invention, there can be provided a user-friendly user interface which can reduce the time required for the optimization of a 3D mesh and which enables a 3D mesh to be edited in a single display environment in an integrated manner.

According to the present invention, there can be provided a user interface which provides a means for enabling a 3D mesh to be directly edited on a 3D image, thereby enabling the determination of a clinician to be directly used in the process of optimizing the 3D mesh.

According to the present invention, there can be provided a user interface which enables a 3D mesh to be intuitively visualized, thus being effective in aiding a clinician to determine the clinical usefulness of the 3D mesh.

According to the present invention, there can be provided a user interface and display method which enable a 3D mesh to be intuitively visualized via various visualization means, thereby facilitating the editing and optimization of the 3D mesh.

According to the present invention, a user can effectively visualize and compare a 3D medical image and 3D mesh information in a single display environment. The information which is useful when a user makes a decision required for the optimization of 3D mesh information is intuitively provided on a 3D medical image. The editing and optimization of a 3D mesh are performed in a single display environment, and thus the time required for the editing and optimization of the 3D mesh can be reduced. The user can directly examine the result of the editing of the 3D mesh on the 3D medical image, and thus there is no need to reciprocate between different display and computing environments. The user can optimize 3D mesh information via a single work process in an integrated environment, and thus the user does not need to suffer from the inconvenience of iteratively reciprocating between a plurality of independent display and computing environments, which has been experienced in the prior arts.

While the present invention has been described in conjunction with the limited embodiments and drawings above, various modifications and variations can be made based on the foregoing description by those having ordinary knowledge in the art to which the present invention pertains. For example, although the described technologies are performed in sequence different from the above-described sequence, the above-described components, such as structures, devices, circuits, units, parts, and the like, are coupled or combined in a form different from the described form, and/or one or more of the components are replaced with other components or equivalents, appropriate results may be achieved.

Therefore, other implementations, other embodiments and equivalents to the claims fall within the scope of the following claims.

What is claimed is:

1. A computing system for displaying medical images, the computing system comprising:
   a display; and
   a processor configured to control image information displayed on the display;
   wherein the processor is configured to:
   receive a medical image of a region of interest (ROI);
   acquire three-dimensional (3D) volume information including segmentation information regarding the ROI of the medical image;
   acquire 3D mesh information corresponding to the ROI;
   generate display information in which the 3D mesh information has been overlaid on the 3D volume information in a 3D space including the 3D volume information, the display information includes the 3D mesh information being overlaid on the 3D volume information based on depth information in a direction of a view such that a first portion of the 3D mesh information located outside the 3D volume information can be visually distinct from a second portion of the 3D mesh information located inside the 3D volume information in the direction of the view; and
   provide a user menu enabling a user to edit the 3D mesh information in the 3D space, and wherein the display information is 3D display information that is represented in the 3D space.

2. The computing system of claim 1, wherein the processor is further configured to generate the display information so that the first portion of the 3D mesh information located outside the 3D volume information can be displayed while having a first visual attribute and the second portion of the 3D mesh information located inside the 3D volume information can be displayed while having a second visual attribute.

3. The computing system of claim 1, wherein the processor is further configured to:
   calculate quantitative information regarding an extent to which a portion of the 3D mesh information has deviated from the 3D volume information; and
   assign a visual attribute based on the quantitative information to the portion of the 3D mesh information.

4. The computing system of claim 1, wherein the processor is further configured to generate the display information by assigning a first visual attribute and a first transparency to the 3D mesh information and assigning a second visual attribute and a second transparency to the 3D volume information.

5. The computing system of claim 1, wherein the processor is further configured to generate an initialized version of the 3D mesh information based on the 3D volume information.

6. The computing system of claim 1, wherein the processor is further configured to generate the 3D mesh information based on a standard model for the ROI.

7. The computing system of claim 6, wherein the processor is further configured to use a personalized standard model based on personal information of a patient and disease diagnosis information regarding the ROI of the patient as the standard model for the ROI.

8. The computing system of claim 1, wherein the processor is further configured to generate an initialized version of the 3D mesh information based on past diagnosis information regarding the ROI of a patient.

9. The computing system of claim 1, further comprising a mesh information storage and management unit configured to store a final version of the 3D mesh information or a history of updated versions of the 3D mesh information.

10. The computing system of claim 1, wherein the processor is further configured to:
    generate updated 3D mesh information by means of an input of the user adapted to modify the 3D mesh information and received in response to the user menu, the user menu enabling the user to edit the 3D mesh information in the 3D space based on the depth information in the direction of the view regarding relative locations of the 3D mesh information to the 3D volume information; and generate the display information so that the updated 3D mesh information can be displayed in place of the 3D mesh information.

11. A method of displaying medical images in a computing system including a display and a processor, the method comprising:

receiving a medical image of a region of interest (ROI);

acquiring three-dimensional (3D) volume information including segmentation information regarding the ROI of the medical image;

acquiring 3D mesh information corresponding to the ROI in a 3D space including the 3D volume information;

generating display information in which the 3D mesh information has been overlaid on the 3D volume information in the 3D space, the 3D mesh information being overlaid on the 3D volume information based on depth information in a direction of a view such that a first portion of the 3D mesh information located outside the 3D volume information can be visually distinct from a second portion of the 3D mesh information located inside the 3D volume information in the direction of the view; and providing a user menu enabling a user to edit the 3D mesh information in the 3D space, wherein the display information is 3D display information that is represented in the 3D space.

12. The method of claim 11, wherein the generating comprises:

dividing the 3D mesh information into the first portion located outside the 3D volume information and the second portion located inside the 3D volume information;

assigning a first visual attribute to the first portion; and assigning a second visual attribute to the second portion.

13. The method of claim 11, wherein the generating comprises:

identifying a portion of the 3D mesh information that has deviated from the 3D volume information;

calculating quantitative information regarding an extent to which the portion of the 3D mesh information has deviated from the 3D volume information; and assigning a visual attribute based on the quantitative information to the deviated portion of the 3D mesh information.

14. The method of claim 11, wherein the generating comprises:

assigning a first visual attribute and a first transparency to the 3D mesh information; and assigning a second visual attribute and a second transparency to the 3D volume information.

15. The method of claim 11, wherein the generating comprises generating an initialized version of the 3D mesh information based on the 3D volume information.

16. The method of claim 11, wherein the generating comprises generating the 3D mesh information based on a standard model for the ROI.

17. The method of claim 11, wherein the generating comprises generating an initialized version of the 3D mesh information based on past diagnosis information regarding the ROI of a patient.

18. The method of claim 11, further comprising storing a final version of the 3D mesh information or a history of updated versions of the 3D mesh information.

19. The method of claim 11, wherein generating display information further comprises:

generating updated 3D mesh information by means of an input of the user adapted to modify the 3D mesh information and received in response to the user menu, the user menu enabling the user to edit the 3D mesh information in the 3D space based on the depth information in the direction of the view regarding relative locations of the 3D mesh information to the 3D volume information; and generating the display information so that the updated 3D mesh information can be displayed in place of the 3D mesh information.

20. A non-transitory computer-readable medium containing program instructions executed by a processor installed in a computing system providing a medical image, the program instructions comprising:

program instructions that receive a medical image of a region of interest (ROI);

program instructions that acquire three-dimensional (3D) volume information including segmentation information regarding the ROI of the medical image;

program instructions that acquire 3D mesh information corresponding to the ROI in a 3D space including the 3D volume information;

program instructions that generate display information in which the 3D mesh information has been overlaid on the 3D volume information in the 3D space, the 3D mesh information being overlaid on the 3D volume information based on depth information in a direction of a view such that a first portion of the 3D mesh information located outside the 3D volume information can be visually distinct from a second portion of the 3D mesh information located inside the 3D volume information in the direction of the view; and program instructions that provide a user menu enabling a user to edit the 3D mesh information in the 3D space, wherein the display information is 3D display information that is represented in the 3D space.

* * * * *